United States Patent
Holmes-Farley et al.

(10) Patent No.: US 6,423,754 B1
(45) Date of Patent: *Jul. 23, 2002

(54) METHOD FOR TREATING HYPERCHOLESTEROLEMIA WITH POLYALLYLAMINE POLYMERS

(75) Inventors: Stephen Randall Holmes-Farley, Arlington; W. Harry Mandeville, III, Lynnfield; Steven K. Burke; Dennis I. Goldberg, both of Sudbury, all of MA (US)

(73) Assignee: GelTex Pharmaceuticals, Inc., Waltham, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/979,096

(22) Filed: Nov. 26, 1997

Related U.S. Application Data

(63) Continuation-in-part of application No. 08/927,247, filed on Sep. 11, 1997, now abandoned, which is a continuation of application No. 08/878,422, filed on Jun. 18, 1997, now abandoned.

(51) Int. Cl.$^7$ ............................ A61P 9/10; A61K 31/785
(52) U.S. Cl. .................. 514/824; 424/78.18; 424/78.27
(58) Field of Search .................. 514/673, 674, 514/824; 424/78.12, 78.18, 78.27

(56) References Cited

U.S. PATENT DOCUMENTS

| | | | |
|---|---|---|---|
| 2,874,132 A | 2/1959 | Riener | 260/2.1 |
| 3,288,770 A | 11/1966 | Butler | 260/88.3 |
| 3,308,020 A | 3/1967 | Wolf et al. | 167/65 |
| 3,383,281 A | 5/1968 | Wolf et al. | 167/65 |

(List continued on next page.)

FOREIGN PATENT DOCUMENTS

| | | |
|---|---|---|
| EP | 0 081 291 | 6/1983 |
| EP | 0 162 388 | 11/1985 |
| EP | 0 373 852 | 6/1990 |
| EP | 0 432 995 | 6/1991 |
| EP | 0 459 632 | 12/1991 |
| GB | 798488 | 7/1958 |
| GB | 1 567 294 | 5/1980 |
| GB | 2 090 605 | 7/1982 |
| GB | 929391 | 6/1993 |
| JP | 6-32178 | 2/1994 |

(List continued on next page.)

OTHER PUBLICATIONS

Chertow, G. M., et al., "Poly[allylamine Hydrochloride] (RenaGel): A Noncalcemic Phosphate Binder for the Treatment of Hyperphosphatemia in Chronic Renal Failure," *American Journal of Kidney Diseases*, 29(1):66–71 (1997).

Burke, S.K., et al., "RenaGel®, a novel calcium–and aluminium–free phosphate binder, inhibits phosphate absorption in normal volunteers," *Nephrol Dial Transplant*, 12:1640–1644 (1997).

(List continued on next page.)

*Primary Examiner*—Edward J. Webman
(74) *Attorney, Agent, or Firm*—Hamilton, Brook, Smith & Reynolds, P.C.

(57) ABSTRACT

A method for removing bile salts from a patient that includes administering to the patient a therapeutically effective amount of a non-absorbable amine polymer characterized by a repeat unit having the formula:

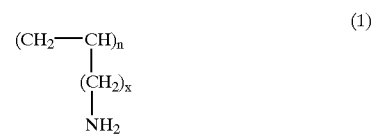

(1)

and salts thereof, where n is a positive integer and x is zero or an integer between 1 and about 4.

3 Claims, 1 Drawing Sheet

U.S. PATENT DOCUMENTS

| | | | |
|---|---|---|---|
| 3,562,266 A | 2/1971 | Minisci et al. .............. | 260/247 |
| 3,692,895 A | 9/1972 | Nelson et al. ................ | 424/78 |
| 3,780,171 A | 12/1973 | Irmscher et al. ............. | 424/79 |
| 3,787,474 A | 1/1974 | Daniels et al. .............. | 260/459 |
| 3,801,641 A | 4/1974 | Payot et al. ......... | 260/567.6 M |
| 3,803,237 A | 4/1974 | Lednicer et al. ........ | 260/584 R |
| 3,980,770 A | 9/1976 | Ingelman et al. ............. | 424/79 |
| 4,027,009 A | 5/1977 | Grier et al. .................... | 424/78 |
| 4,071,478 A | 1/1978 | Shen et al. ................. | 260/2 R |
| 4,098,726 A | 7/1978 | Wagner et al. .............. | 528/403 |
| 4,101,461 A | 7/1978 | Strop et al. ................... | 521/32 |
| 4,111,859 A | 9/1978 | Strop et al. ................... | 521/33 |
| 4,205,064 A | 5/1980 | Wagner et al. ................ | 424/78 |
| 4,217,429 A | 8/1980 | Wagner et al. .............. | 525/411 |
| 4,340,585 A | 7/1982 | Borzatta et al. ............. | 424/79 |
| 4,426,489 A | 1/1984 | Wessling et al. ............ | 524/815 |
| 4,528,347 A | 7/1985 | Harada ........................ | 526/219 |
| 4,540,760 A | 9/1985 | Harada et al. .............. | 526/211 |
| 4,557,930 A | 12/1985 | Kihara et al. ................ | 424/79 |
| 4,559,391 A | 12/1985 | Ueda et al. ................ | 525/366 |
| 4,605,701 A | 8/1986 | Harada et al. .............. | 525/107 |
| 4,680,360 A | 7/1987 | Ueda et al. ................ | 526/310 |
| 4,759,923 A | 7/1988 | Buntin et al. .............. | 424/440 |
| 5,055,197 A | 10/1991 | Albright et al. ............ | 210/638 |
| 5,189,111 A | 2/1993 | Danner .................... | 525/328.2 |
| 5,236,701 A | 8/1993 | St. Pierre et al. ............. | 424/78 |
| 5,374,422 A | 12/1994 | St. Pierre et al. ........ | 424/78.12 |
| 5,414,068 A | 5/1995 | Bliem et al. ................ | 528/288 |
| 5,428,112 A | 6/1995 | Ahlers et al. ............ | 525/326.7 |
| 5,430,110 A | 7/1995 | Ahlers et al. ............ | 525/328.2 |
| 5,451,397 A | 9/1995 | Albright et al. ......... | 424/78.01 |
| 5,462,730 A | 10/1995 | McTaggart et al. ...... | 424/78.35 |
| 5,487,888 A | 1/1996 | Mandeville et al. ....... | 424/78.1 |
| 5,496,545 A | 3/1996 | Holmes-Farley et al. | 424/78.11 |
| 5,607,669 A * | 3/1997 | Mandeville, III et al. ................ | 424/78.12 |
| 5,624,963 A * | 4/1997 | Mandeville, III et al. ... | 514/789 |

FOREIGN PATENT DOCUMENTS

| | | |
|---|---|---|
| WO | WO91/18027 | 11/1991 |
| WO | WO92/10522 | 6/1992 |
| WO | WO94/04596 | 3/1994 |
| WO | WO94/27620 | 12/1994 |
| WO | WO95/34585 | 12/1995 |
| WO | WO 95/34585 | 12/1995 |
| WO | WO 95/34588 | 12/1995 |
| WO | WO96/39449 | 12/1996 |

OTHER PUBLICATIONS

Burke, S.K., et al., "RenaGel™, A Calcium and Aluminium Free Phosphate Binder, Inhibits Phosphate Absorption in Normal Volunteers," *Abstracts Book* from: XXXIII Congress of the European Renal Association European Dialysis and Transplant Associate, (Jun. 18, 1996).

Burke, S.K., et al., "RenaGel™, A Calcuim and Aluminium Free Phosphate Binder, Lowers Serum Phosphorus Hemodialysis Patients," *Abstracts Book* from: XXXIII Congress of the European Renal Association European Dialysis and Transplant Associate, (Jun. 18, 1996).

English Translation of Japanese Patent Laid–Open No. Hei 6–321786, Translated by Hosoda International Patent Office. (1994).

Kobayashi, Kazuo and Oka, Takayuki, "Polyamines for inhibition of intestinal absorption of bile acids," *Chemical Abstracts* 122(13) 27 Mar. 1995, Abstract No. 151392, XP002077304.

Heming, A.E. and Flanagan, Thomas L., "Considerations in the Selection of Cation Exchange Resins for Therapeutic Use," *Annals of the New York Academy of Sciences*, 57:239–251 (1954).

McCarthy, Peter A., "New Approaches to Atherosclerosis: An Overview," *Medicinal Research Reviews*, 13(2):139–159 (1993).

Butler, G.B. and Do, C.H., "Comblike Cyclopolymers of Alkyldiallylamines and Alkyldiallylmethammonium Chlorides," in *Water–Soluble Polymers*, eds. Shalaby, McCormick & Butler, Chapter 9, pp. 151–158 ACS Symposium Series 467 (1991).

Dubin, P.L. and Davis, D.D., "Quasi–Elastic Light Scattering of Polyelectrolyte–Micelle Complexes," *Macromolecules 17*: 1294–1296 (1984).

Wang, G.–J. and Engberts, J., "Fluorescence probing of the formation of hydrophobic microdomains by cross–linked poly(alkylmethyldiallylammonium bromides) in aqueous solution," *Recl. Trav. Chim. Pays–Bas 113*, 390–393 (1994).

Kunitake, T., et al., "Catalyses of Polymer Complexes. 4. Polysoap–Catalyzed Decarboxylation of 6–Nitrobenzisoxazole–3–carboxylate Anion. Importance of the Hydrophobic Environment in Activation of the Anion," *J. Org. Chem 42*(2): 306–312 (1977).

Wang, G.–J. and Engberts, J., "Study of the Conformational State of Non–Cross–Linked and Cross–Linked Poly(alkylmethyldiallylammonium Chlorides) in Aqueous Solution by Fluorescence Probing," *Gazzetta Chimica Italiana*, 125: 393–397 (1995).

Kuron, G.W., et al., "the Bile Acid Binding and Hypocholesterolemic Action of Two–Water–Soluble Polymers," *Atherosclerosis*, 37 353–360 (1980).

Harada, S. and Arai, K., "The Cyclo–copolymerization of Diallyl Compounds and Sulfur Dioxide," *Die Makromolekulare Chemie 107*: 64–93 (1967).

Wang, G.–J. and Engberts, J., "Induction of Aggregate Formation of Cationic Polysoaps and Surfactants by Low Concentrations of Additives in Aqueous Solution," *Langmuir*, 10(8): 2583–2587 (1994).

Wang, G.–J. and Engberts, J., "Synthesis of Hydrophobically and Electrostatically Modified Polyacrylamides and Their Catalytic Effects on the Unimolecular Decarboxylation of 6–Nitrobenzisoxazole–3–carboxylate Anion," *Langmuir*, 11(10): 3856–3861 (1995).

Wang, G.–J. and Engberts, J., "Synthesis and Catalytic Properties of Non–Cross–Linked and Cross–Linked Poly-(alkylmethyldiallylammonium bromides) Having Decyl, Octyl, and Hexyl Side Chains," *J. Org. Chem*, 60: 4030–4038 (1995).

Kevelam, J., et al., "Polymer–Surfactant Interactions Studied by Titration Microcalorimetry: Influence of Polymer Hydrophobicity, Electrostatic Forces, and Surfactant Aggregational State," *Langmiur*, 12(20): 4709–4717 (1996).

Wang, G.–J. and Engberts, J., "Synthesis and Catalytic Properties of Cross–Linked Hydrophobically Associating Poly(alkylmethyldiallylammonium bromides)," *J. Org. Chem.*, 59(15): 4076–4081 (1994).

Yang, Y.J. and Engberts, J., "Synthesis and Catalytic Properties of Hydrophobically Modified Poly(alkylmethyldiallylammonium bromides)," *J. Org. Chem.*, 56: 4300–4304 (1991).

Negi, Y., et al., "Cyclopolymerization of Diallylamine Derivatives in Dimethyl Sulfoxide," *J. of Polymer Science: Part A–1*, 5: 1951–1965 (1967).

Hodgkin, H. et al., "Use of $^{13}$C–NMR in the Study of Reactions on Crosslinked Resins," Published by John Wiley & Sons, *J. of Polymer Science: Polymer Chemistry Edition*, 19(5): 1239–1249 (1981).

Yeh, F., et al., "Nanoscale Supramolecular Structures in the Gels of Poly(Diallyldimethylammonium Chloride) Interacting with Sodium Dodecyl Sulfate," *J. Am. Chem. Soc.*, 118(28): 6615–6618 (1996).

Boothe, J.E., et al., "Some Homo–and Copolymerization Studies of Dimethyldiallylammonium Chloride," *J. Macromol. Sci.–Chem.*, A4(6): 1419–1430 (1970).

\* cited by examiner

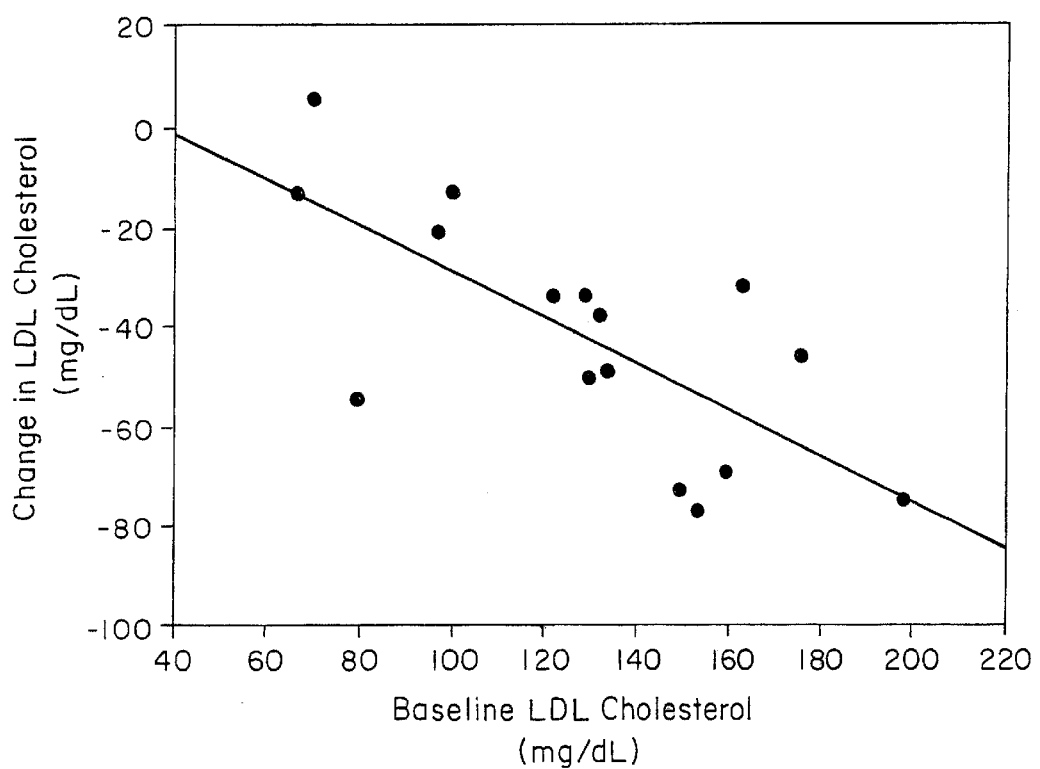

METHOD FOR TREATING HYPERCHOLESTEROLEMIA WITH POLYALLYLAMINE POLYMERS

RELATED APPLICATION

This application is a Continuation-in-Part of U.S. Application No.: 08/927,247 filed Sep. 11, 1997; now abandoned, which is a Continuation of U.S. Ser. No.: 08/878,422, now abandoned, filed Jun. 18, 1997, the entire teachings of which are incorporated herein by reference.

BACKGROUND OF THE INVENTION

Reabsorption of bile acids-from the intestine conserves lipoprotein cholesterol in the bloodstream. Conversely, blood cholesterol levels can be diminished by reducing reabsorption of bile acids.

One method of reducing the amount of bile acids that are reabsorbed and, thus, reducing serum cholesterol is the oral administration of compounds that sequester the bile acids and cannot themselves be absorbed. The sequestered bile acids consequently are excreted.

Compounds which have been suggested for bile acid sequestration include various ion exchange polymers. One such polymer is cholestyramine, a copolymer of divinylbenzene/styrene and trimethylammonium methylstyrene. It has been long recognized that this polymer is unpalatable, gritty, and constipating. More recently, various polymers have been suggested which are characterized by hydrophobic substituents and quaternary ammonium radicals substituted upon an amine polymer backbone (Ahlers, et al. U.S. Pat. Nos. 5,428,112 and 5,430,110 and McTaggert, et al., U.S. Pat. 5,462,730, which are incorporated herein by reference).

Thus, there is still a need to discover superior bile acid sequestrants.

SUMMARY OF THE INVENTION

The invention relates to the unexpected discovery that a new class of ion exchange resins have improved bile salt sequestration properties resulting in reduced dosages, which improve patient tolerance and compliance, thereby improving the palatability of the composition and are relatively easy to manufacture. The polymers, employed in the invention comprise non-absorbable, and optionally cross-linked polyamines as defined herein. The properties of the polymer which gave rise to the present invention were discovered during clinical trials of the polymer for its use in binding phosphate in patients suffering from hyperphosphatemia. The polyamines of the invention are characterized by one or more monomeric units of the formula:

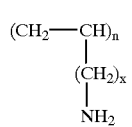

(1)

and salts thereof, where n is a positive integer and x is 0 or an integer between 1 and about 4. The polymer can be characterized by the substantial absence of one or more alkylated amine monomers and/or the substantial absence of one or more trialkylammonium alkyl groups. In preferred embodiments, the polymer is crosslinked by means of a multifunctional crosslinking agent.

The invention provides an effective treatment for removing bile salts from a patient (and thereby reducing the patient's cholesterol level), particularly in patients with a serum LDL level of at least about 130 mg/dL. The invention also provides for the use of the polymers described herein for the manufacture of a.medicament for the treatment of hypercholesterolemia or for bile acid sequestration.

Other features and advantages will be apparent from the following description of the preferred embodiments thereof and from the claims.

BRIEF DESCRIPTION OF THE DRAWING

The FIGURE presents the effect of cross-linked polyallylamine on LDL cholesterol relative to baseline LDL cholesterol.

DETAILED DESCRIPTION OF THE INVENTION

As described above, the polymers employed in the invention comprise, optionally cross-linked polyamines characterized by the formula above. Preferred polymers are polyallylamine or polyvinylamine. Importantly, the polymers can be characterized by the substantial absence of substituted or unsubstituted alkyl substituents on the amino group of the monomer, such as obtained in the alkylation of an amine polymer. That is, the polymer can be characterized in that the polymer is substantially free of alkylated amine monomers.

The polymer can be a homopolymer or a copolymer of one or more amine-containing monomers or non-amine containing monomers. Where copolymers are manufactured with the monomer of the above formula, the comonomers are preferably inert, non-toxic and/or possess bile acid sequestration properties. Examples of suitable non-amine-containing monomers include vinylalcohol, acrylic acid, acrylamide, and vinylformamide. Examples of amine. containing monomers preferably include monomers having the Formula 1 above. Preferably, the monomers are aliphatic. Most preferably, the polymer is a homopolymer, such as a homopolyallylamine or homopolyvinylamine.

Preferably, the polymer is rendered water-insoluble by crosslinking. The cross-linking agent can be characterized by functional groups which react with the amino group of the monomer. Alternatively, the crosslinking group can be characterized by two ore more vinyl groups.which undergo free radical polymerization with the amine monomer.

Examples of suitable crosslinking agents include acryloyl chloride, epichlorohydrin, butanedioldiglycidyl ether, ethanedioldiglycidyl ether, and dimethyl succinate.

A preferred crosslinking agent is epichlorohydrin because of its high availability and low cost. Epichlorohydrin is also advantageous because of it's low molecular weight and hydrophilic nature, maintaining the water-swellability of the polyamine gel.

The level of crosslinking makes the polymers insoluble and substantially resistant to absorption and degradation, thereby limiting the activity of the polymer to the gastrointestinal tract. Thus, the compositions are non-systemic in their activity and will lead to reduced side-effects in the patient. Typically, the cross-linking agent is present in an amount from about 0.5–25% (more preferably about 2.5–20% and most preferably 1–10%) by weight, based upon total weight of monomer plus crosslinking agent.

Typically, the amount of crosslinking agent that is reacted with the amine polymer is sufficient to cause between about 0.5 and twenty percent of the amines. In a preferred embodiment, between about 0.5 and 20 percent of the amine groups react with the crosslinking agent.

Preferred polymers of the invention are generally known in the art. Holmes-Farley, et al. (U.S. Pat. No. 5,496,545), describes the use of aliphatic amine polymers in the treatment of hyperphosphatemia. These polymers have also been suggested for use in the treatment of iron-overload (Mandeville, et al., U.S. Pat. No. 5,487,888). The teachings of both of these patents are incorporated herein by reference.

Non-cross-linked and cross-linked polyallylamine and polyvinylamine are generally known in the art and/or are commercially available. Methods for the manufacture of polyallylamine and, polyvinylamine, and cross-linked derivatives thereof, are described in the above US Patents, the teachings of which are incorporated entirely by reference. Harada et al. (U.S. Pat. Nos. 4,605,701 and 4,528,347, which are incorporated herein by reference in their entirety) also describe methods of manufacturing polyallylamine and cross-linked polyallylamine.

As described above the polymer can be administered in the form of a salt. By "salt" it is meant that the nitrogen group-in the repeat unit is protonated to create a positively charged nitrogen atom associated with a negatively charged counterion.

The cationic counterions can be selected to minimize adverse effects on the patient, as is more particularly described below. Examples of suitable counterions include $Cl^-$, $Br^-$, $CH_3OSO_3^-$, $HSO_4^-$, $SO_4^{2-}$, $HCO_3^-$, $CO_3^-$, acetate, lactate, succinate,.propionate, butyrate, ascorbate, citrate, maleate, folate, an amino acid derivative, a nucleotide, a lipid, or a phospholipid. The counterions can be the same as, or different from, each other. For example, the reaction product can contain two different types of counterions, both of which are exchanged for the bile salts being removed.

The polymers according to the invention can be administered orally to a patient in a dosage of about 1 mg/kg/day to about 1 g/kg/day, preferably between about 5 mg/kg/day to about 200 mg/kg/day (such as between about 10 mg/kg/day to about 200 mg/kg/day); the particular dosage will depend on the individual patient (e.g., the patient's weight and the extent of bile salt removal required). The polymer can be administered either in hydrated or dehydrated form, and can be flavored or added to a food or drink, if desired to enhance patient acceptability. Additional ingredients such as other bile acid sequestrants, drugs for treating hypercholesterolemia, atherosclerosis or other related indications, or inert ingredients, such as artificial coloring agents can be added as well.

Examples of suitable forms for administration include tablets, capsules, and powders (e.g., for sprinkling on food) or mixing in water or juice). The tablet, capsule, or powder can be coated with a substance capable of protecting the composition from disintegration in the esophagus but will allow disintegration as the composition in the stomach and mixing with food to pass into the patient's small intestine. The polymer can be administered alone or in combination with a pharmaceutically acceptable carrier substance, e.g., magnesium carbonate, lactose, or a phospholipid with which the polymer can form a micelle.

The invention can be used to treat patients, preferably humans, with hypercholesterolemia, particularly patients with a serum LDL level which exceeds about 130 mg/dL.

The invention will now be described more specifically by the examples.

EXAMPLES

A. Polymer Preparation

1. Preparation of Poly(vinylamine)

The first step involved the preparation of ethylidenebisacetamide. Acetamide (118 g), acetaldehyde (44.06 g), copper acetate (0.2 g), and water (300 mL) were placed in a 1 L three neck flask fitted with condenser, thermometer, and mechanical stirred. Concentrated HCl (34 mL) was added and the mixture was heated to 45–50° C. with stirring for 24 hours. The water was then removed in vacuo to leave a thick sludge which formed crystals on cooling to 5° C. Acetone (200 mL) was added and stirred for a few minutes, after which the solid was filtered off and discarded. The acetone was cooled to 0° C. and solid was filtered off. This solid was rinsed in 500 mL acetone and air dried 18 hours to yield 31.5 g of ethylidenebis-acetamide.

The next step involved the preparation of vinylacetamide from ethylidenebisacetamide. Ethylidenebisacetamide (31.05 g), calcium carbonate (2 g) and celite 541 (2 g) were placed in a 500 mL three neck flask fitted with a thermometer, a mechanical stirred, and a distilling heat atop a Vigroux column. The mixture was vacuum distilled at 24 mm Hg by heating the pot to 180–225° C. Only a single fraction was collected (10.8 g) which contained a large portion of acetamide in addition to the product (determined by NMR). This solid product was dissolved in isoprpopanol (30 mL) to form the crude vinylacetamide solution used for polymerization.

Crude vinylacetamide solution (15 mL), divinylbenzene (1 g, technical grade, 55% pure, mixed isomers), and AIBN (0.3 g) were mixed and heated to reflux under a nitrogen atmosphere for 90 minutes, forming a solid precipitate. The solution was cooled, isopropanol (50 mL) was added, and the solid was collected by centrifugation. The solid was rinsed twice in isopropanol, once in water, and dried in a vacuum oven to yield 0.8 g of poly(vinylacetamide), which was used to prepare poly(vinylamine).

Poly(vinylacetamide) (0.79 g) was placed in a 100 mL one neck flask containing water (25 mL) and conc. HCl (25 mL). The mixture was refluxed for 5 days, after which the solid was filtered off, rinsed once in water, twice in isopropanol, and dried in a vacuum oven to yield 0.77 g of product. Infrared spectroscopy indicated that a significant amount of the amide (1656 $cm^{-1}$) remained and that not much amine (1606 $cm^{-1}$) was formed. The product of this reaction (~0.84 g) was suspended in NaOH (46 g) and water (46 g) and heated to boiling (~140° C.). Due to foaming the temperature was reduced and maintained at ~100° C. for 2 hours. Water (100 mL) was added and the solid collected by filtration. After rinsing once in water the solid was suspended in water (500 mL) and adjusted to pH 5 with acetic acid. The solid was again filtered off, rinsed with water, then isopropanol, and dried in a vacuum oven to yield 0.51 g of product. Infrared spectroscopy indicated that significant amine had been formed.

2. Preparation of Poly(allylamine) Hydrochloride

To a 2 liter, water-jacketed reaction kettle equipped with (1) a condenser topped with a nitrogen gas inlet, (2) a thermometer, and (3) a mechanical stirrer was added concentrated hydrochloric acid (360 mL). The acid was cooled to 5° C. using circulating water in the jacket of the reaction kettle (water temperature =0° C.). Allylamine (328.5 mL, 250 g) was added dropwise with stirring while maintaining the reaction temperature at 5–10° C. After addition was complete, the mixture was removed, placed in a 3 liter one-neck flask, and 206 g of liquid was removed by rotary vacuum evaporation at 60° C. Water (20 mL) was then added and the liquid was returned to the reaction kettle. Azobis (amidinopropane) dihydrochloride (0.5 g) suspended in 11 mL of water was then added. The resulting reaction mixture was heated to 50° C. under a nitrogen atmosphere with stirring for 24 hours. Additional azobis(amidinopropane) dihydrochloride (5 mL) suspended in 11 mL of water was then added, after which heating and stirring were continued for an additional 44 hours.

At the end of this period, distilled water (100 mL) was added to the reaction mixture and the liquid mixture allowed to cool with stirring. The mixture was then removed and placed in a 2 liter separatory funnel, after which it was added dropwise to a stirring solution of methanol (4 L), causing a solid to form. The solid was removed by filtration, re-suspended in methanol (4 L), stirred for 1 hour, and collected by filtration. The methanol rinse was then repeated one more time and the solid dried in a vacuum oven to afford 215.1 g of poly(allylamine) hydrochloride as a granular white solid.

3. Preparation of Poly(allylamine) Hydrochloride Crosslinked with Epichlorohydrin To a 5 gallon vessel was added poly(allylamine) hydrochloride prepared as described in Example 2 (1 kg) and water (4 L). The mixture was stirred to dissolve the hydrochloride and the pH was adjusted by adding solid NaOH (284 g). The resulting solution was cooled to room temperature, after which epichlorohydrin crosslinking agent (50 mL) was added all at once with stirring. The resulting mixture was stirred gently until it gelled (about 35 minutes). The crosslinking reaction was allowed to proceed for an additional 18 hours at room temperature, after which the polymer gel was removed and placed in portions in a blender with a total of 10 L of water. Each portion was blended gently for about 3 minutes to form coarse particles which were then stirred for 1 hour and collected by filtration. The solid was rinsed three times by suspending it in water (10 L, 15 L, 20 L), stirring each suspension for 1 hour, and collecting the solid each time by filtration. The resulting solid was then rinsed once by suspending it in isopropanol (17 L), stirring the mixture for 1 hour, and then collecting the solid by filtration, after which the solid was dried in a vacuum oven at 50° C. for 18 hours to yield about 677 g of the cross linked polymer as a granular, brittle, white solid.

4. Preparation of Poly(allylamine) Hydrochloride Crosslinked with Butanedioldiglycidyl Ether To a 5 gallon vessle was added poly(allylamine) hydrochloride prepared as described in Example 2 (500 g) and water (2 L). The mixture was stirred to dissolve the hydrochloride and the pH was adjusted to 10 by adding solid NaOH (134.6 g). The resulting solution was cooled to room temperature in the vessel, after which 1,4-butanedioldiglycidyl ether crosslinking agent (65 mL) was added all at once with stirring. The resulting mixture was stirred gently until it gelled (about 6 minutes). The crosslinking reaction was allowed to proceed for an additional 18 hours at room temperature, after which the polymer gel was removed and dried in a vacuum oven at 75° C. for 24 hours. The dry solid was then ground and sieved to −30 mesh, after which it was suspended in 6 gallons of. water and stirred for 1 hour. The solid was then filtered off and the rinse process repeated two more times. The resulting solid was then air dried for 48 hours, followed by drying in a vacuum oven at 50° C. for 24 hours to yield about 415 g of the crosslinked polymer as a white solid.

5. Preparation of Poly(allylamine) Hydrochloride Crosslinked with Ethanedioldiglycidyl Ether To a 100 mL beaker was added poly(allylamine) hydrochloride prepared as described in Example 2 (10 g) and water (40 mL). The mixture was stirred to dissolve the hydrochloride and the pH was adjusted to 10 by adding solid NaOH. The resulting solution was cooled to room temperature in the beaker, after which 1,2-ethanedioldiglycidyl ether crosslinking agent (2.0 mL) was added all at once with stirring. The resulting mixture was stirred gently until it gelled (about 4 minutes). The crosslinking reaction was allowed to proceed for an additional 18 hours at room temperature, after which the polymer gel was removed and blended in 500 mL of methanol. The solid was then filtered off and suspended in water (500 mL). After stirring for 1 hour, the solid was filtered off and the rinse process repeated. The resulting solid was rinsed twice in isopropanol (400 mL) and then dried in a vacuum oven at 50° C. for 24 hours to yield 8.7 g of the crosslinked polymer as a white solid.

6. Preparation of Poly(allylamine) Hydrochloride Crosslinked with Dimethylsuccinate To a 500 mL round-bottomed flask was added poly(allylamine) hydrochloride prepared as described in Example 2 (10 g), methanol (100 mL), and triethylamine (10 mL). The mixture was stirred and dimethylsuccinate crosslinking agent (1 mL) was added. The solution was heated to reflux and the stirring discontinued after 30 minutes. After 18 hours, the solution was cooled to room temperature, and the solid filtered off and blended in 400 mL of isopropanol. The solid was then filtered off and suspended in water (1 L). After stirring for 1 hour, the solid was filtered off and the rinse process repeated two more times. The solid was then rinsed once in isopropanol (800 mL) and dried in a vacuum oven at 50° C. for 24 hours to yield 5.9 g of the crosslinked polymer as a white solid.

An aqueous solution of poly(allylamine hydrochloride) (550 lb of a 50.7% aqueous solution) was diluted with water (751 lb) and neutralized with aqueous sodium hydroxide (171 lb of a 50% aqueous solution). The solution was cooled to approximately 25° C. and acetonitrile (1340 lb) and epichlorohydrin (26.2 lb) were added. The solution was stirred vigorously for 21 hours. During this time, the reactor contents changed from two liquid phases to a slurry of particles in a liquid. The solid gel product was isolated by filtration. The gel was washed in an elutriation process with water (136,708 lb). The gel was isolated by filtration and rinsed with isopropanol. The gel was slurried with isopropanol (1269 lb) and isolated by filtration. The isopropanol/water wet gel was dried in a vacuum dryer at 60° C. The dried product was ground to pass through a 50 mesh screen to give a product suitable for pharmacologic use (166 lb, 73%).

7. Effect on Serum Cholesterol Levels in Humans

Hemodialysis patients on stable doses of calcium and/or aluminum based phosphate binders entered a one-week screening period. The phosphate binders were discontinued.

Those patients developing hyperphosphatemia (serum P04>6.0 mg/dL) during the wash-out period were eligible for drug treatment. A RenaGel® binder (epichlorohydrin cross-linked polyallylamine, GelTex Pharmaceuticals, Inc., Waltham, Ma.) starting dose was based on the degree of hyperphosphatemia. Starting doses were either two, three, or four 465 mg capsules three times per day with meals. At the end of each of three subsequent two week periods, the dose of RenaGel® binder was increased by one capsule per meal as necessary to achieve a serum phosphorus between 2.5 and 5.5 mg/dL, inclusive. If the serum phosphorus fell to less than 2.5 mg/dL, the RenaGel® binder dose was decreased by one to three capsules per day to elevate the serum phosphorus to above 2.5 mg/dL.

When the serum calcium fell below normal (defined by the central laboratory normal range) during the study, the serum calcium level was returned to within the normal range by adding an evening calcium supplement of up to 1,000 mg of elemental calcium as the carbonate salt on an empty stomach at bedtime or the dialysate calcium concentration was increased. TUMS EX® 750 mg tablets containing 300 mg of elemental calcium were provided. Other brands of calcium carbonate or calcium acetate were used if the patient prefered another formulation.

At the conclusion of the treatment period, any remaining RenaGel® capsules were retrieved and the patient was kept off phosphate binder for two weeks. After this second wash-out period, patients discontinued any evening calcium supplements and returned to their original phosphate binders.

Approximately 216 hemodialysis patients on stable doses of phosphate binders were entered into the study. The patients had to have well controlled serum phosphorus and not have any clinically significant unstable medical conditions. Only those patients who were hyperphosphatemic (serum P04<6.0 mg/dL) during the first washout period (approximately 180 patients) received treatment.

The polymer was supplied as capsules containing 500 mg of polymer. Each patient started on one of three doses of polymer: (i) 2 capsules (0.93 g) three times per day with meals; (ii) 3 capsules (1.4 g) three times per day with meals; and (iii) 4 capsules (1.86 g) three times per day with meals.

| Parameter | Visit | Overall | | | | Dose Level*** | | | | | | |
|---|---|---|---|---|---|---|---|---|---|---|---|---|
| | | | | | | Low | | Medium | | High | | |
| | | N | Mean | Std Dev | P-Value* | N | mean | Std Dev | N | Mean | Std Dev | N | Mean | Std Dev | Value** |
| Total Cholesterol (mg/dL) | −1 | 28 | 214.6 | 41.2 | | 13 | 217.0 | 42.4 | 3 | 267.3 | 57.4 | 12 | 198.8 | 23.8 | 0.0978 |
| | 2 | 29 | 221.7 | 35.6 | | 13 | 216.5 | 35.0 | 4 | 261.8 | 46.1 | 12 | 214.0 | 25.1 | 0.0790 |
| | 6 | 28 | 182.2 | 46.2 | | 12 | 186.8 | 44.1 | 4 | 234.8 | 63.1 | 12 | 160.1 | 25.6 | 0.0222 |
| | 10 | 25 | 184.7 | 48.5 | | 12 | 195.5 | 47.7 | 4 | 223.5 | 52.9 | 9 | 153.1 | 29.0 | 0.0181 |
| | 10/Final | 25 | 184.7 | 48.5 | | 12 | 195.5 | 47.7 | 4 | 223.5 | 52.9 | 9 | 153.1 | 29.0 | 0.0181 |
| | Change (10/Final − 2) | 25 | −37.2 | 29.0 | <0.0001 | 12 | −22.3 | 27.3 | 4 | −38.3 | 25.3 | 9 | −56.7 | 22.3 | 0.0098 |
| | 12 | 25 | 208.1 | 42.1 | | 12 | 202.6 | 38.4 | 4 | 267.3 | 45.6 | 9 | 189.2 | 18.0 | 0.0291 |
| | Change (12 − 10) | 24 | 23.1 | 34.2 | 0.0006 | 12 | 7.1 | 40.7 | 4 | 43.8 | 12.9 | 8 | 36.8 | 16.2 | 0.0306 |
| LDL Cholesterol (mg/dL) | −1 | 27 | 145.0 | 34.1 | | 12 | 147.2 | 32.2 | 3 | 191.1 | 40.2 | 12 | 131.2 | 24.9 | 0.0494 |
| | 2 | 29 | 154.6 | 27.4 | | 13 | 147.4 | 16.3 | 4 | 184.6 | 46.2 | 12 | 152.3 | 25.3 | 0.1441 |
| | 6 | 28 | 110.5 | 33.4 | | 12 | 113.3 | 32.4 | 4 | 150.5 | 43.9 | 12 | 94.5 | 17.3 | 0.0085 |
| | 10 | 25 | 109.0 | 37.7 | | 12 | 109.5 | 34.6 | 4 | 141.0 | 45.6 | 9 | 94.2 | 32.7 | 0.1750 |
| | 10/Final | 25 | 109.0 | 37.7 | | 12 | 109.5 | 34.6 | 4 | 141.0 | 45.6 | 9 | 94.2 | 32.7 | 0.1750 |
| | Change (10/Final − 2) | 25 | −45.7 | 29.3 | <0.0001 | 12 | −38.0 | 29.0 | 4 | −43.6 | 28.0 | 9 | −56.8 | 29.9 | 0.2972 |
| | 12 | 25 | 141.0 | 33.6 | | 12 | 132.3 | 20.9 | 4 | 194.2 | 37.9 | 9 | 129.0 | 23.8 | 0.0221 |
| | Change (12 − 10) | 24 | 33.0 | 24.8 | <0.0001 | 12 | 22.8 | 23.6 | 4 | 53.2 | 17.9 | 8 | 38.2 | 23.9 | 0.0503 |
| HDL Cholesterol (mg/dL) | −1 | 27 | 37.6 | 9.4 | | 12 | 39.6 | 10.1 | 3 | 32.7 | 4.7 | 12 | 36.8 | 9.6 | 0.5108 |
| | 2 | 29 | 36.4 | 9.2 | | 13 | 37.8 | 9.8 | 4 | 31.3 | 5.0 | 12 | 36.5 | 9.6 | 0.4077 |
| | 6 | 28 | 38.5 | 10.5 | | 12 | 40.3 | 13.1 | 4 | 37.0 | 7.4 | 12 | 37.3 | 8.6 | 0.6622 |
| | 10 | 25 | 36.5 | 11.1 | | 12 | 41.3 | 12.0 | 4 | 34.5 | 6.1 | 9 | 30.9 | 9.3 | 0.1053 |
| | 10/Final | 25 | 36.5 | 11.1 | | 12 | 41.3 | 12.0 | 4 | 34.5 | 6.1 | 9 | 30.9 | 9.3 | 0.1053 |
| | Change (10/Final − 2) | 25 | 0.8 | 9.0 | 0.2823 | 12 | 2.8 | 10.3 | 4 | 3.3 | 3.0 | 9 | −3.0 | 8.2 | 0.1000 |
| | 12 | 25 | 38.6 | 11.3 | | 12 | 42.0 | 10.1 | 4 | 35.5 | 5.3 | 9 | 35.6 | 14.2 | 0.1986 |
| | Change (12 − 10) | 24 | 0.9 | 8.5 | 0.8018 | 12 | 0.7 | 7.7 | 4 | 1.0 | 2.7 | 8 | 1.3 | 11.8 | 0.7914 |
| Triglycerides (mg/dL) | −1 | 28 | 165.8 | 80.5 | | 13 | 164.7 | 93.9 | 3 | 217.7 | 113.0 | 12 | 153.9 | 55.3 | 0.5796 |
| | 2 | 29 | 153.9 | 92.3 | | 13 | 156.3 | 103.7 | 4 | 229.5 | 104.0 | 12 | 126.2 | 64.0 | 0.2165 |
| | 6 | 28 | 165.5 | 89.5 | | 12 | 165.7 | 80.8 | 4 | 236.5 | 123.4 | 12 | 141.7 | 80.7 | 0.2408 |
| | 10 | 25 | 196.2 | 165.3 | | 12 | 223.4 | 222.6 | 4 | 240.0 | 65.1 | 9 | 140.3 | 81.8 | 0.0994 |
| | 10/Final | 25 | 196.2 | 165.3 | | 12 | 223.4 | 222.6 | 4 | 240.0 | 65.1 | 9 | 140.3 | 81.8 | 0.0994 |
| | Change (10/Final − 2) | 25 | 38.2 | 150.6 | 0.3161 | 12 | 64.3 | 214.4 | 4 | 10.5 | 55.2 | 9 | 15.8 | 41.0 | 0.9199 |
| | 12 | 25 | 142.5 | 91.2 | | 12 | 141.7 | 107.2 | 4 | 188.0 | 76.3 | 9 | 123.4 | 74.3 | 0.2964 |
| | Change (12 − 10) | 24 | −54.0 | 151.3 | 0.0135 | 12 | −81.8 | 209.6 | 4 | −52.0 | 34.7 | 8 | −13.4 | 49.7 | 0.2320 |

*Wilcoxon Signed Rank Test
**Kruskal-Wallis Exact Test
***Dose level defined using the last actual dose during study 8. Egfect in Healthy Young and Old, Male and Female Volunteers Weekly throughout this period, on Mondays (MWF patients) and Tuesdays (TTS patients), the patients gave blood for the laboratory studies just prior to dialysis. On the Wednesdays (MWF patients) and Thursdays (TTS patients) of the same weeks, the investigator inquired if the patient experienced any adverse events or had changes in medications that might indicate adverse events and reviewed the results of the laboratory tests.

Dietary intakes of phosphorus were assessed on selected days in the first wash-out, treatment, and second wash-out periods by 24-hour recall methods by nutritionists from the University of Massachusetts Medical Center.

Eight young (19–40 years of age) and eight old (65 years of age and older) healthy volunteer male and female subjects received 2.325 grams of RenaGel® binder (epichlorohydrin cross-linked polyallylamine) three times per day with meals for 32 days. All drug doses were administered with meals served at a clinical research center for the entire 32 day study. On day 0, a 10 mL blood sample was drawn prior to the morning meal and analyzed for plasma cholesterol levels. On day 32 a second 10 mL blood sample was drawn prior to the morning meal. Subjects were released from the study after the morning meal on day 32. Plasma triglycerides and HDL were measured and LDL cholesterol was calculated by the Friedewald formula.

The Figure presents the effect of the polymer on LDL cholesterol relative to baseline LDL cholesterol. The higher the baseline cholesterol in these normal volunteers, the greater the decline in LDL cholesterol. LDL cholesterol declined by a mean of 42 mg/dL for the entire 16 patient cohort. Five patients in the study had baseline LDL cholesterol lower than 100 mg/dL. The decline in LDL cholesterol in the 11 patients with baseline LDL cholesterol >than 120 mg/dL was 52.5 mg/dL.

EQUIVALENTS

Those skilled in the art will know, or be able to ascertain, using no more than routine experimentation, many equivalents to the specific embodiments of the invention described herein. These and all other equivalents are intended to be encompassed by the following claims.

What is claimed is:

1. A method for removing bile salts from a patient comprising administering to said patient a therapeutically effective amount of one or more crosslinking homopolymers characterized by a repeat unit having the formula:

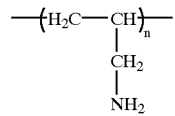

and salts thereof, wherein n is a positive integer and said polymer is crosslinked with a crosslinking agent having functional groups which react with the amino group of the repeat unit, and which is present in an amount from about 2.5–25% by weight based upon the combined weight of monomer and crosslinking agent and characterized in that the polymer is free of alkylated amine monomers.

2. The method of claim 1 wherein said crosslinking agent comprises epichlorohydrin.

3. The method of claim 1 wherein the patient has a serum LDL level of at least 130 mg/dL.

* * * * *